United States Patent [19]

Clement

[11] Patent Number: 5,409,013

[45] Date of Patent: Apr. 25, 1995

[54] TISSUE REMOVAL ASSEMBLY

[75] Inventor: Thomas P. Clement, Bloomington, Ind.

[73] Assignee: Mectra Labs, Inc., Bloomfield, Ind.

[21] Appl. No.: 830,580

[22] Filed: Feb. 4, 1992

Related U.S. Application Data

[63] Continuation-in-part of Ser. No. 580,945, Sep. 11, 1990, abandoned, which is a continuation-in-part of Ser. No. 432,084, Nov. 6, 1989, Pat. No. 5,019,054.

[51] Int. Cl.$^6$ .............................................. A61B 10/00
[52] U.S. Cl. .................................................. 128/753
[58] Field of Search .............................. 128/751—755; 606/14–16, 170, 171

[56] References Cited

U.S. PATENT DOCUMENTS

| | | |
|---|---|---|
| 628,907 | 7/1899 | Hart . |
| 786,215 | 3/1905 | Hepnar . |
| 811,111 | 1/1906 | Wegefarth ............... 604/32 |
| 1,585,934 | 5/1926 | Muir . |
| 2,437,329 | 3/1948 | Moore . |
| 2,715,899 | 8/1955 | MacLean . |
| 2,812,765 | 11/1957 | Tofflemire . |
| 3,012,752 | 12/1961 | Buck . |
| 3,081,770 | 3/1963 | Hunter . |
| 3,109,426 | 11/1963 | Noonan et al. . |
| 3,157,201 | 11/1964 | Littmann . |
| 3,173,414 | 3/1965 | Guillant ............... 128/752 |
| 3,368,734 | 1/1983 | Banko . |
| 3,434,691 | 3/1969 | Hamilton . |
| 3,467,082 | 9/1969 | Gilbert ............... 604/248 |
| 3,682,177 | 8/1972 | Ames et al. ............... 128/310 |
| 3,735,751 | 5/1973 | Katz . |
| 3,783,900 | 1/1974 | Waldbillig . |
| 3,788,602 | 1/1974 | Kitzie ............... 251/312 |
| 3,794,032 | 2/1974 | Derouineau . |
| 3,833,000 | 9/1974 | Bridgman . |
| 3,834,372 | 9/1974 | Turney . |
| 3,837,345 | 9/1974 | Matar . |
| 3,853,127 | 12/1974 | Spademan . |
| 3,902,498 | 9/1975 | Niederer . |
| 3,957,082 | 5/1976 | Fuson et al. . |
| 3,994,287 | 11/1976 | Turp et al. ............... 128/6 |
| 3,995,619 | 12/1976 | Glatzer . |
| 4,011,869 | 3/1977 | Seiler, Jr. . |
| 4,016,881 | 4/1977 | Rioux et al. . |
| 4,037,599 | 7/1977 | Raulerson . |
| 4,043,322 | 8/1977 | Robinson . |
| 4,073,297 | 2/1978 | Kopp . |

(List continued on next page.)

FOREIGN PATENT DOCUMENTS

| | | |
|---|---|---|
| 0350291 | 5/1989 | European Pat. Off. . |
| 2332743 | 6/1977 | France ............... 128/753 |
| 3528656 | 7/1986 | Germany . |
| 991478 | 5/1965 | United Kingdom . |

OTHER PUBLICATIONS

K. Semm, "Pelviscopy-Operative Guidelines", Kiel, Germany, 1988, pp. 53–54.

(List continued on next page.)

*Primary Examiner*—Max Hindenburg
*Attorney, Agent, or Firm*—Barnes & Thornburg

[57] ABSTRACT

A suction and irrigation lavage with a cannula having a distal end insertible into a patient's body, with a cutting edge for capture of body tissue in the cannula interior and a hollow cutter moveable relative to the cannula for cutting body tissue captured by the cutting edge. A conduit piece is rigidly attached to the cannula and supports the cutter for movement, and has a channel defined in communication with the hollow interior of the cutter. A source of suction is connected to: the conduit piece channel by a dual purpose valve for withdrawing body tissue cut by the cutter through the cannula and conduit piece; and a source of irrigation fluid for passing fluid into the patient. The conduit has a hand grip portion for positioning the distal end of the cannula to a desired location in a patient while at the same time allowing for a digit of the hand to actuate the valve to control passage of irrigation fluid or suction to the cannula if desired. A tool entry conduit is located within the cutter and extends outwardly of the conduit piece in a direction away from the cannula for permitting entry of a surgical tool into the conduit piece and the hollow cutter.

32 Claims, 3 Drawing Sheets

U.S. PATENT DOCUMENTS

| | | |
|---|---|---|
| 4,079,737 | 3/1978 | Miller . |
| 4,099,529 | 7/1978 | Peyman . |
| 4,111,207 | 9/1978 | Seiler, Jr. . |
| 4,173,328 | 11/1979 | Karbo .................................. 251/317 |
| 4,177,814 | 12/1979 | Knepshield et al. . |
| 4,198,959 | 4/1980 | Otani ...................................... 128/5 |
| 4,210,146 | 7/1980 | Banko . |
| 4,230,128 | 10/1980 | Aramayo . |
| 4,240,411 | 12/1980 | Hosono .................................. 128/4 |
| 4,261,357 | 4/1981 | Kontos . |
| 4,280,498 | 7/1981 | Jensen . |
| 4,282,873 | 8/1981 | Roth . |
| 4,282,884 | 8/1981 | Boebel .................................. 128/751 |
| 4,299,217 | 11/1981 | Sagae et al. . |
| 4,314,560 | 2/1982 | Helfgott et al. . |
| 4,314,586 | 2/1982 | Folkman ............................... 251/309 |
| 4,379,458 | 4/1983 | Bauer et al. ......................... 604/264 |
| 4,397,355 | 8/1983 | Doblar et al. . |
| 4,400,168 | 8/1983 | Buechel et al. ....................... 604/48 |
| 4,414,974 | 11/1983 | Dotson et al. . |
| 4,430,081 | 2/1984 | Timmermans ....................... 604/256 |
| 4,443,220 | 4/1984 | Hauer et al. ......................... 604/408 |
| 4,444,184 | 4/1984 | Oretorp ................................ 128/305 |
| 4,445,517 | 5/1984 | Feild ..................................... 128/752 |
| 4,468,216 | 8/1984 | Muto ...................................... 604/43 |
| 4,491,132 | 1/1985 | Aikins . |
| 4,512,344 | 4/1985 | Barber . |
| 4,519,385 | 5/1985 | Atkinson et al. . |
| 4,531,935 | 7/1985 | Berryessa ............................. 604/45 |
| 4,540,156 | 9/1985 | Cross ..................................... 251/309 |
| 4,552,146 | 11/1985 | Jensen et al. . |
| 4,553,957 | 11/1985 | Williams et al. ...................... 604/43 |
| 4,553,964 | 11/1985 | Sasaki . |
| 4,566,480 | 1/1986 | Parham . |
| 4,568,332 | 2/1986 | Shippert ............................... 604/119 |
| 4,577,629 | 3/1986 | Martinez . |
| 4,581,014 | 4/1986 | Millerd et al. . |
| 4,589,414 | 5/1986 | Yoshida et al. ....................... 604/22 |
| 4,593,717 | 6/1986 | Levasseur . |
| 4,595,005 | 6/1986 | Jinotti .................................... 604/32 |
| 4,642,090 | 2/1987 | Utrata .................................... 604/22 |
| 4,642,097 | 2/1987 | Siposs . |
| 4,643,197 | 2/1987 | Greene et al. ....................... 128/762 |
| 4,644,951 | 2/1987 | Bays . |
| 4,645,496 | 2/1987 | Oscarsson ............................ 604/248 |
| 4,648,868 | 3/1987 | Hardwick et al. . |
| 4,651,753 | 3/1987 | Lifton .................................... 128/751 |
| 4,654,027 | 3/1987 | Dragan et al. . |
| 4,662,871 | 5/1987 | Rafelson .............................. 604/119 |
| 4,667,927 | 5/1987 | Oscarsson ............................ 251/209 |
| 4,674,500 | 6/1987 | DeSatnick ............................. 604/22 |
| 4,676,242 | 6/1987 | Doi ....................................... 128/398 |
| 4,681,123 | 7/1987 | Valtchev .............................. 128/753 |
| 4,690,672 | 9/1987 | Veltrup .................................. 604/43 |
| 4,692,140 | 9/1987 | Olson ..................................... 604/40 |
| 4,702,260 | 10/1987 | Wang .................................... 128/753 |
| 4,708,147 | 11/1987 | Haaga ................................... 128/753 |
| 4,715,360 | 12/1987 | Akui et al. ............................. 128/4 |
| 4,735,606 | 4/1988 | Davison . |
| 4,758,235 | 7/1988 | Tu . |
| 4,793,359 | 12/1988 | Sharrow ............................... 128/658 |
| 4,807,666 | 2/1989 | Morse .................................. 251/309 |
| 4,808,155 | 2/1989 | Mahurkar ............................... 604/43 |
| 4,810,244 | 3/1989 | Allen ....................................... 604/44 |
| 4,881,550 | 11/1989 | Kothe ................................... 128/752 |
| 4,900,300 | 2/1990 | Lee ......................................... 604/22 |
| 4,911,202 | 3/1990 | Nelson ................................. 137/595 |
| 4,925,450 | 5/1990 | Imonti et al. ........................ 604/240 |
| 4,932,957 | 6/1990 | Zwick . |
| 4,958,621 | 9/1990 | Topel et al. . |
| 4,966,551 | 10/1990 | Betush . |
| 4,994,067 | 2/1991 | Summers ............................. 606/159 |
| 4,994,079 | 2/1991 | Genese et al. ....................... 606/206 |
| 5,019,035 | 5/1991 | Missirlian et al. .................... 604/22 |
| 5,019,054 | 5/1991 | Clement et al. . |
| 5,053,044 | 10/1991 | Mueller et al. . |
| 5,078,688 | 1/1992 | Lobodzinski et al. . |
| 5,106,364 | 4/1992 | Hayafuji et al. ....................... 604/22 |
| 5,273,524 | 12/1993 | Fox et al. . |
| 5,275,609 | 1/1994 | Pingleton et al. . |

OTHER PUBLICATIONS

Pentax Precision Instrument Corp., "Gastrofiberscope", Surgical Products, Mar. 1990, vol. 9, No. 6, p. 13.

Storz, "Laparoscopic Cholecystectomy for the General Surgeon–Its Time has Come", Surgica Products, May 1990, vol. 9, No. 6, p. 13.

Pentax Precision Instrument Corp., "GI Fiberscopes", Surgical Products, May 1990, vol. 9, No. 6, p. 13.

Healthco International Handbook, 1990, p. 116.

Storz The World of Endoscopy, Semm Instruments for Operative Pelviscopy, 4th Edition, Mar. 1987, pp. 1–4.

Richard Wolf cat. pg. and sketch/admitted prior art Jan. 1992.

American Surgical Instruments, Inc., "Nexhat–Dorsey (List continued on next page.)

OTHER PUBLICATIONS

Disposable Hydro–Dissection Trumpet Valve", 3 Sheets, Mar. 19, 1990.

Richard Wolf, "The Complete Endoscopy Manufacturer", Surgical Products, May 1990. vol. 9, No. 6, p. 20.

Johnson & Johnson Medical Inc., "CIDEX is safe for scopes. Don't take our word for it.", Surgical Products, May 1990, vol. 9, No. 6, p. 25.

Pentax®, "Pentax® PNEII Bronchofiberscopes", Surgical Products, May 1990, vol. 9, No. 6, p. 44.

Pentax Precision Instrument Corp., "Therapeutic Gastrofiberscope with Water Jet", Sep. 1990, vol. 10, No. 1, p. 39.

Cabot Medical, "Suction/Irrigation Probe", Surgical Products, Nov. 1990, vol. 10, No. 11, p. 29.

EndoDynamics, Inc., "Aspiration Device", Surgical Products, Nov. 1990, vol. 10, No. 11, p. 30.

"Irrigation/Aspiration Probe", Surgical Products, Sep. 1990, vol. 10, No. 11, p. 28.

Cabot Medical, "Larparoscopic Cholecystectomy From the Company Who Knows Laparoscopy", Surgical Products, Jan. 1991, vol. 10, No. 3, p. 4.

Olympus, "The Olympus Laparoscopic Cholecystectomy System: Resolution for Gallstones, with the leader in High–Resolution Optics", Surgical Products, Jan. 1990, vol. 10, No. 3, p. 8.

Apple Medical, "Hunt/Reich Secondary Cannula", Surgical Products, May 1991, vol. 10, No. 7, p. 5.

Baxter Healthcare Corp., "Infusion Pump", Surgical Products, Jun. 1991, vol. 10, No. 8, p. 32.

Core Dynamics TM Inc., "Disposable Trocar with Reusable Cannula", Surgical Products, Jun. 1991, vol. 10, No. 8, p. 4.

Dexide catalog page and sketch 1991.

Halkey Roberts catalog 1990 3 pages.

TISSUE REMOVAL ASSEMBLY

This is a continuation in part application of U.S. application Ser. No. 07/580,945, for Clement et al., filed Sep. 11, 1990 abandoned, which is a continuation in part of U.S. application Ser. No. 07/432,084, filed Nov. 6, 1989, and now U.S. Pat. No. 5,019,054, to Clement et al., issued May 28, 1991.

The present invention relates to a surgical assembly for removing body tissue for disposal or analysis. More particularly, the present invention includes a cannula having a tip configured to allow cutting, laser vaporization, and mechanical or hydraulic cutting with high pressure fluids of body tissue during endoscopic, laparoscopic, or other surgical procedures.

Removal of tissue from a patient's body for disposal or analysis is commonly required in surgical procedures. Typically, cutting instruments have been used to separate small portions of tissue from the patient's body, and grasping or suction devices are used to retrieve the tissue. For removal of small organs or tissue in laparoscopic or endoscopic surgical procedures, combination instruments that combine cutting and suction functions are known. Such dual function cutting/suction instruments can include a cutting instrument disposed inside a tube having a notch or other opening to permit the cutting instrument to have selective access to body tissue.

Notched cannulas having internally driven cutting tubes to cut tissue are known. For example, U.S. Pat. No. 4,099,529 to Peyman; U.S. Pat. Nos. 4,111,207 and 4,011,869 to Seiler, Jr.; and U.S. Pat. No. 4,589,414 to Yoshida et al. all describe surgical cutting instruments terminating in cannula having a notch.

The present invention provides a surgical assembly for removal of body tissue. Preferably, the entire assembly is used a single time, and is constructed from low-cost, easily disposable materials. The surgical assembly includes a cannula defining a cannula interior, with the cannula having a proximal end and a distal end. During a surgical operation, the distal end of the cannula is inserted into a patient's body. A notch is defined at the distal end of the cannula to permit access to the cannula interior. This notch is positioned between oppositely directed first and second catches that are configured to assist capture and retention of body tissue in the cannula interior. In practice, tissue is snagged by one of the catches, and then maneuvered into the notch prior to removal of the tissue from the body.

Tissue is removed from the body with the aid of a cutter movable in the cannula interior to cut body tissue that has been maneuvered through the notch into the cannula interior. Preferably, a tube is attached to the cutter. This tube defines a tube interior into which a fiber optic cable can be situated to convey laser energy for vaporization of body tissue. The tube and attached cutter are linked to a movable assembly that is configured to be movable with respect to the cannula. The movable assembly defines a passage therethrough in fluid communication with the tube interior. This passageway can optionally be sealed with an attached, breachable seal.

In other preferred embodiments, a conduit piece is attached to the cannula. The conduit piece has at least one channel defined therein in fluid communication with the cannula interior, and in addition the conduit piece movably supports the movable assembly. To enhance versatility and ease of use of the surgical assembly, a handheld rotary valve is connected to the conduit piece to control fluid flow in the at least one channel. The handheld rotary valve is configured to provide an easily graspable pistol grip.

Body tissue cut by the cutter, or vapor and fumes created by laser destruction of body tissue, can be drawn by suction away from the distal end of the cannula interior, through the at least one channel of the conduit piece. Body tissue can be directly passed from the at least one channel of the conduit piece, through the rotary valve, and into a chamber for medical waste. Alternatively, the rotary valve can be set to direct the body tissue to a tissue sample chamber that allows storage of body tissue for later analysis.

Other objects and advantages of the invention will become apparent from the following description of a preferred embodiment presently perceived as the best mode for practice of the invention and consideration of the accompanying drawings.

DETAILED DESCRIPTION OF THE DRAWINGS

Figures 1, 2:
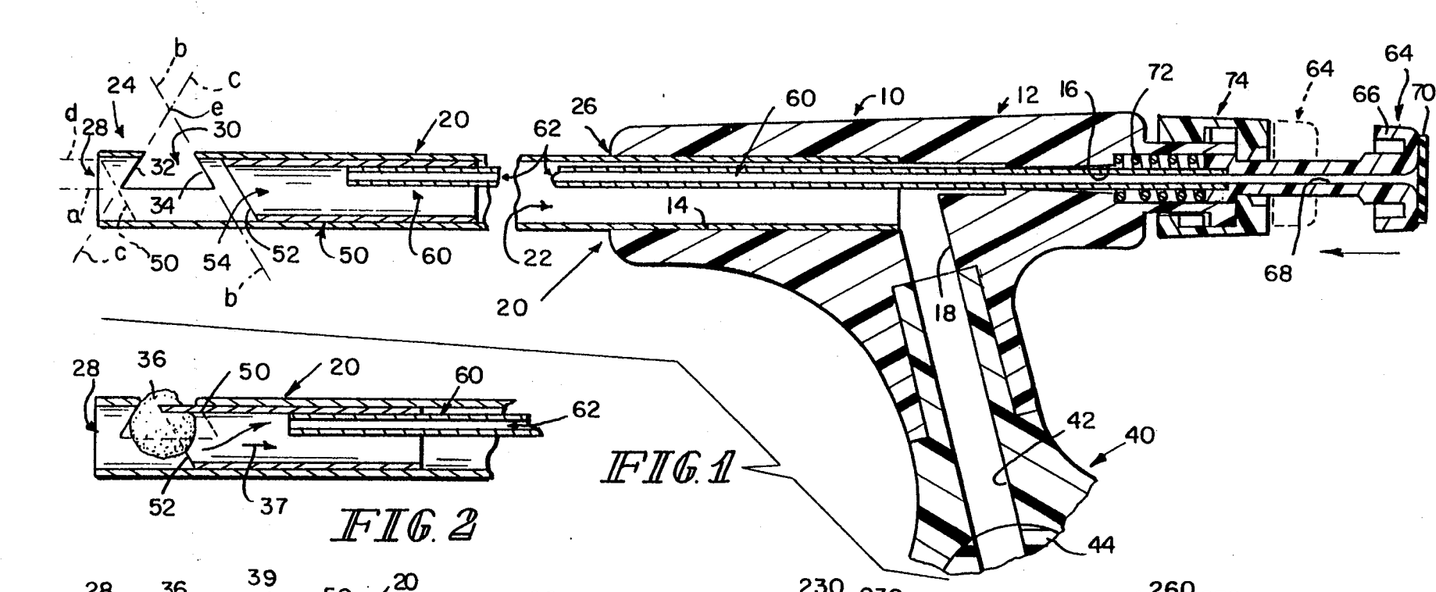
FIG. 1 is a cross sectional side view of a tissue removal assembly including a cannula with a notch defined in its distal end, and a pair of oppositely directed catches located on either side of the notch to assist in capture of tissue, the cannula being attached to a conduit piece at its proximal end. A cutter is movably positioned in a cannula interior of the cannula, and a handheld rotary valve (partially shown) extends from the conduit piece to provide a pistol-type grip.
FIG. 2 is a cross sectional side view of the distal end of the cannula illustrated in FIG. 1, showing the position of tissue caught with the oppositely directed catches and maneuvered into the cannula interior through the notch to allow tissue dissection and removal for analysis or disposal of small pieces of tissue.

As best illustrated in FIG. 1, a tissue removal assembly 10 useful for laparoscopic, endoscopic, or other surgical procedures includes a conduit piece 12 interconnecting a cannula 20 and a handheld rotary valve 40. Suitable handheld rotary valves are described in U.S. Pat. No. 5,019,054, to Clement et al., issued May 28, 1991, and assigned to Mectra, Inc., the disclosure of which is herein incorporated by reference. Typically, a surgeon supports the assembly 10 with one hand holding the handheld rotary valve 40, leaving the other hand free for manipulation of other instruments. The tissue removal assembly 10 is useful for removing small organs, scar tissue, growths, biopsy samples, or other tissue from a patient's body. The tissue removal assembly 10 can be used to destroy tissue at an operative site by laser ablation, or can alternatively be used to cut away tissue for later analysis or disposal.

In preferred embodiments, the tissue removal assembly 10 is disposed of after a single use, minimizing problems related to sterilization, storage, and maintenance of reusable instruments. Construction from low cost, easily incinerated or disposed of materials, which may include molded plastics, is contemplated.

The conduit piece 12 is formed to internally define a first channel 14, a second channel 16, and a third channel 18. All three channels 14, 16, and 18 substantially define respective cylindrical volumes, with first channel 14 having a slightly greater inner diameter than the second channel 16. The third channel 18 has an inner diameter intermediate between that of the first and second channels 14 and 16. The first channel 14 and second channel 16 are connected in fluid communication, and are colinearly defined to allow straight passage therethrough of linearly extending objects. The third channel 18 is also in fluid communication with channels 14 and 16, and connects substantially perpendicular to and between the channels 14 and 16. As will be appreciated with reference to FIG. 1, the interconnections between the channels 14, 16, and 18 can be characterized as a "T-type" connection. However, provision of "Y"-type connections or other arrangements known in the art for fluid interconnection of channels 14, 16, and 18 is contemplated.

As shown in FIG. 1, the cannula 20 extends longitudinally in a straight line, although curved, bent, flexible, or other conventional cannula designs are also contemplated. The cannula 20 has a distal end 24 for insertion into a patient's body and a proximal end 26 connected to the conduit piece 12. The distal end 24 of the cannula 20 terminates in a tip opening 28 that allows entrance or egress of solids, liquids, or gasses from a cannula interior 22 defined by the cannula 20. The cannula interior 22 is defined between the respective distal end proximal ends 24 and 26 of the cannula 20 to accept and allow bidirectional passage therethrough of solids, liquids, or gasses. Fluids, instruments, or gasses can be introduced from the proximal end 26 for effective operation in a patient's body at the distal end 24, or fluid (blood, etc.), solids (such as tissue samples), or gasses (such as may be produced by laser ablation and vaporization) at the operating site can be withdrawn from the distal end 24 through the cannula interior 22.

The cannula 20 is dimensioned to conformably fit into the first channel 14 of the conduit piece 12, and is rigidly held in position by adhesives, welding, friction tight fit, or other suitable attachment mechanism to the conduit piece 12. Since the proximal end 26 of the cannula 20 is held within the first channel 14, fluid communication (as well as passage of medical instruments or tissue samples) is maintained between the second and third channels 16 and 18, and the cannula interior 22.

The distal end 24 of the cannula 20 is configured to assist in capture and retention of body tissue 36 at an operating site in a patient's body. As is illustrated in FIG. 1, a notch 30 is defined in the distal end 24 of the cannula 20, immediately adjacent to the tip opening 28 of the cannula 20. Like the tip opening 28, the notch 30 allows access to the cannula interior 22. The notch 30 is cut in the cannula 20 to define a first catch 32 and an oppositely directed second catch 34. As illustrated in FIG. 1, the notch 30 is formed by removal of a portion of the distal end 24 of the cannula 20. Two cuts into cannula 20 are made along oppositely directed planes indicated by lines b and c (planes b and c both extend perpendicular to the page in the illustration). The cuts along planes b and c terminate at their respective intersection with longitudinally directed planes indicated by lines a and d (planes a and d also extend perpendicular to the page). When a line of intersection between planes b and c is defined outside the cannula 20 (the line extends perpendicular to the page and is represented by a point e), a dihedral angle bc between planes b and c is defined. Typically, the dihedral angle bc is between about 30 degrees and 150 degrees, and is illustrated in FIG. 1 as about 60 degrees.

In practice, the notch 30 and catches 32 and 34 can be easily formed by three cuts into the cannula 20 along planes a, b, and c. More complex cutting, forming, molding, or castings can also be used to provide catches of differing shape. In addition, instead of forming catches from the body of the cannula, it is also contemplated to provide oppositely directed catches attached or affixed to a cannula adjacent to a notch. Multiple catches or several notches may also be used to enhance tissue grabbing or retention effectiveness.

In operation, as illustrated in FIG. 2, catches 32 and 34 enhance tissue grabbing and holding effectiveness, allowing a surgeon to maneuver the distal end 24 to catch and hold a piece of body tissue 36. After body tissue 36 has been positioned in the notch 30, a cutter 50 can be moved forward from its position in the cannula interior 22 toward the distal end 24 of the cannula 20 to cut and/or assist in retaining tissue in the notch 30.

As illustrated in FIG. 1, the cutter 50 has a substantially tubular configuration, defining a cutter passageway 54 therethrough. In addition, the distally directed end of the cutter 50 has a sharpened edge 52. To enhance cutting efficiency, the sharpened edge 52 is created by a traverse, slanting, and non-perpendicular cut across the cutter 50. The resultant elliptically shaped cylinder edge is sharpened to give a beveled edge, with the bevel being directed inward toward the cannula interior 22. Of course, perpendicular cuts across a cutter to give a circular edge, or other cutter edge configurations apparent to those skilled in the art may be substituted for the illustrated cutter embodiment.

The cutter 50 is sized to snugly fit into the cannula interior 22, with its outer diameter being slightly less than the inner diameter of the cannula 20. As illustrated in FIG. 2, when tissue has been engaged by catches 32 and 34 and maneuvered into the cannula interior 22 through the notch 30, the cutter 50 is moved forward from its normal position on the proximal side of the notch 30 in the cannula interior 22, to a cutting position in the region of the notch 30 (position of cutter 50 indicated by dotted outline). When the cutter 50 passes through the cannula interior 22 to cover the region of the notch 30 (adjacent to tip opening 28) any tissue entrapped in the cannula interior 22 is severed by the sharpened edge 52. This severed, dissected tissue can be drawn by surgical instruments, or preferably by suction pressure, through the cutter passageway 54, toward the distal end 24 of the cannula interior 22, into the third channel 18 of the conduit piece 12 and through the handheld rotary valve 40 to a storage or disposal site.

The cutter 50 is moved by a movable assembly 64. The movable assembly 64 includes a button 66 that defines a passageway 68 therethrough. The passageway 68 is breachably sealed by seal 70 in adhesive or welded attachment to the button 66. A tube 60, having a tube interior 62, is attached to extend between the cutter 50 and the button 66. Movement of the button 66 toward the conduit piece 12 consequently causes the cutter 50 to move toward the distal end 24 of the cannula 20.

The cutter 50 is moved back toward the proximal end 26 of the cannula 20 by action of an expansion spring 72. The expansion spring 72 is biasably positioned between the conduit piece 12 and the button 66 to press the button 66 away from the conduit piece 12. When the button 66 is not manually pressed toward the conduit piece 12, this outward (away from the conduit 12) biased force is resisted by a block 74 attached to the conduit piece 12 and configured to partially surround button 66. The spring arrangement is configured to promote manually operated reciprocating motion, with the rest, or normal, position of the cutter 50 (attached by way of tube 60 to the button 66) selected to be on the proximal side of the notch 30, leaving the notch 30 normally open to accept body tissue. Of course, as those skilled in the art will appreciate, it is alternatively contemplated to reverse the biased spring direction, so that a cutter 50 is normally positioned on the distal side of the notch, with the cutter having its proximal edge sharpened.

Figure 3:
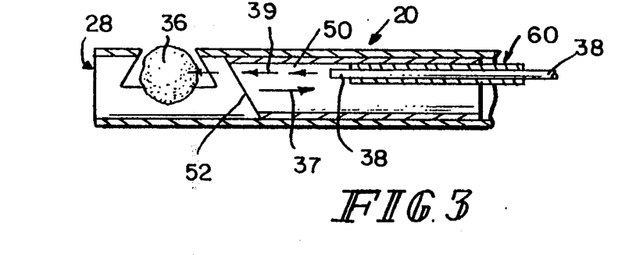
FIG. 3 is a cross sectional side view of the distal end of the cannula illustrated in FIGS. 1 and 2, showing positioning of a fiber optic cable in a tube interior of a tube attached to the cutter, the fiber optic cable acting to convey laser energy for vaporization of tissue positioned in the cannula interior.

In addition to separation of tissue from a patient's body by cutting action of the cutter 50, tissue can optionally be removed by application of laser energy to ablate and vaporize tissue. As illustrated in FIG. 1 and FIG. 3, delivery of laser energy (indicated by arrows 39 in FIG. 3) to tissue 36 is enabled by passage of fiber optic cable 38 inserted, respectively, through breachable seal 70, passageway 68 of button 66 (seal 70 and button 66 illustrated in FIG. 1), and tube interior 62 of tube 60. In operation, the tissue 36 is maneuvered into position through the notch 30, and laser energy is transmitted through the fiber optic cable 38 from a UV laser light source (not shown) to vaporize the tissue 36.

Figure 4:
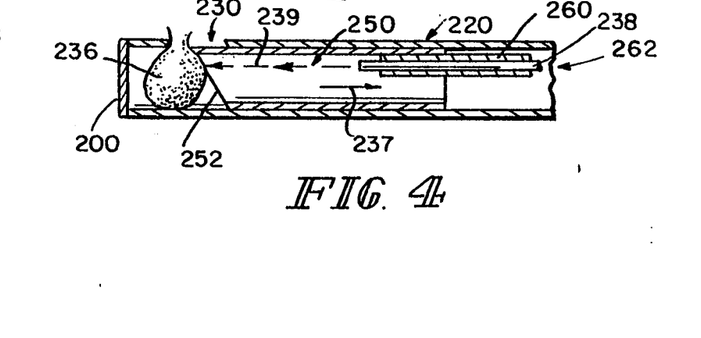
FIG. 4 is a side cross sectional view of an alternative embodiment of a distal end for a cannula such as is illustrated in FIGS. 1-3. In this embodiment, the tip of the cannula is closed to present a laser energy absorbing or dissipating surface that reduces the risk of inadvertent burning or vaporization of tissue.

An alternative cannula tip embodiment suitable for dual mechanical cutter/laser removal of tissue is illustrated in FIG. 4. A cannula 220 (substantially similar to cannula 20) having a notch 230 therein is used to entrap tissue 236. The distal end of the cannula 220 is closed with a tip wall 200. The tip wall 200 can be coated or otherwise prepared to have a laser absorptive or dissipative surface that reduces back reflection of laser energy transferred through fiber optic cable 238 (positioned in tube interior 262 of tube 260) to the tissue 236. In operation, after the tissue 236 is firmly positioned in the notch 230, the cutter 250 can be moved forward to substantially cover the notch 230. This reduces escape of fumes or burned tissue into the patient's body. Of course, the cutter 250 can still alternatively be used without recourse to laser energy to dissect and remove tissue.

Figure 5:
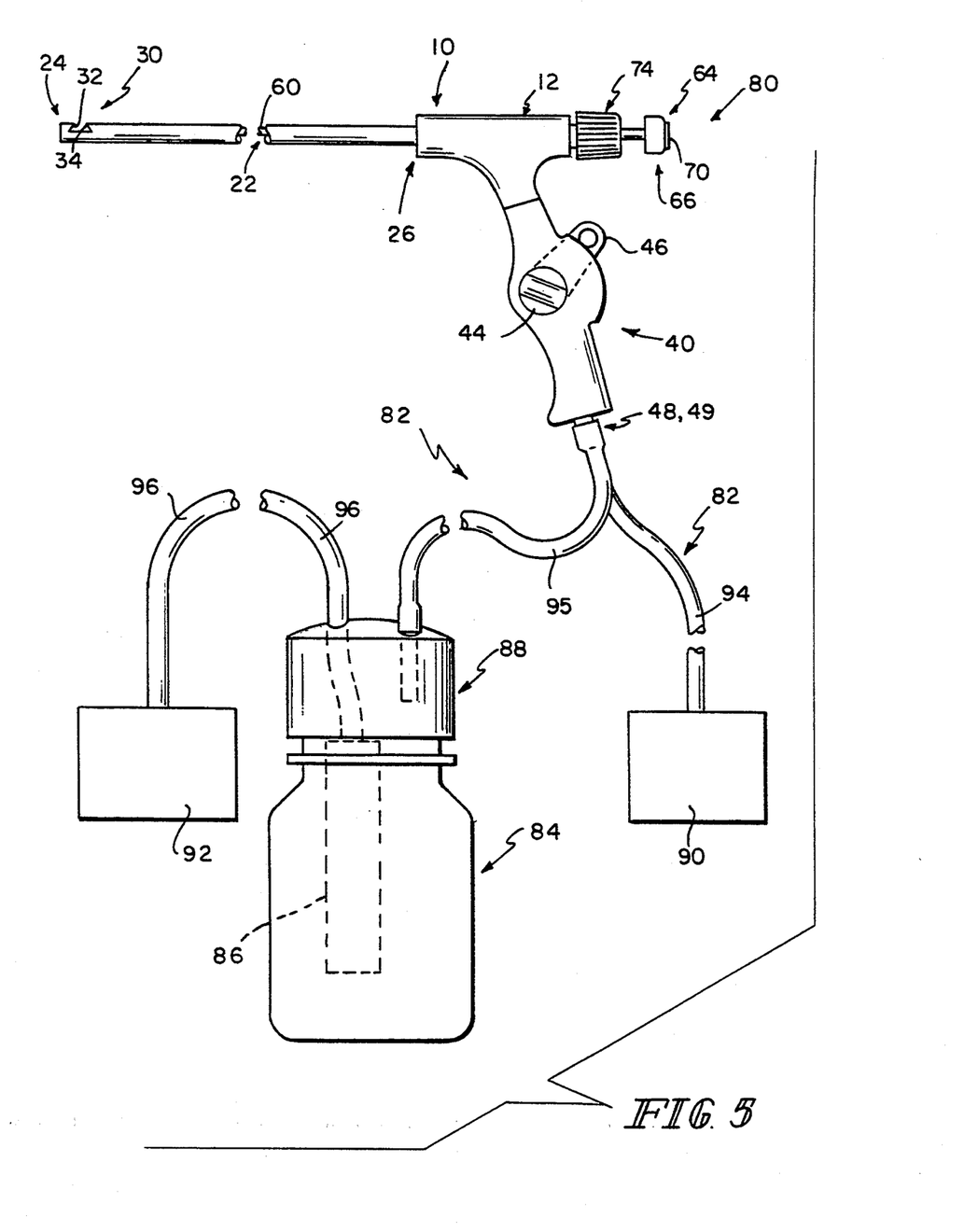
FIG. 5 is a schematic view of a tissue removal system, illustrating the tissue removal assembly of FIG. 1 connected to a tissue sample trap assembly that includes a tissue sample container connected to a vacuum source.

Dissected tissue or fumes from vaporized tissue are removed from the cannula by suction (indicated by arrow 37 in FIGS. 2-3, and arrow 237 in FIG. 4) produced by fluid connection to one of vacuum sources 90 and 92 illustrated in FIG. 5. As illustrated in FIG. 5 a tissue removal system 80 includes a tissue storage apparatus 82 connected to tissue removal assembly 10 such as previously described. The tissue storage apparatus 82 includes a sample container 84, conduits 94, 95, 96, and vacuum sources 90 and 92. Conduit 94 is connected in fluid communication between inlet 49 of the rotary valve 40 and vacuum source 90. Conduit 95 is connected in fluid communication between inlet 48 of the dual inlet port rotary valve 40 and vacuum source 92. Conduit 96 is connected to a screen 86 positioned inside sample container 84, allowing fluid communication between the sample container 84 and vacuum source 92 but limiting passage of solid tissue samples.

In operation, disposal of tissue samples entrained in the cannula interior 22 of the cannula 20 involves turning the handle 46 of the rotary valve 40 to bring the rotor 44 into a position that allows fluid communication between vacuum source 90 and cannula interior 22. Solid, liquid, or gas waste that is present in the cannula interior 22 are drawn by suction toward the proximal end 26 of the cannula 20, and through the third channel 18 into the rotary valve 40. The wastes continue through the conduit 94 and into the vacuum source 90 for disposal.

If samples of tissue are desired for analysis, the handle 46 of the rotary valve 40 is turned to bring the rotor 44 into a position that allows fluid communication between vacuum source 92 and cannula interior 22. A solid tissue sample dissected from a patient's body and present in the cannula interior 22 are drawn by suction toward the proximal end 26 of the cannula 20, and through the third channel 18 into the rotary valve 40. The sample is drawn by suction through the conduit 95 and into the sample container 84 for storage. Continued passage of the sample (not shown) through the conduit 96 and into vacuum source 92 is prevented by a screen 86 that allows fluid flow but prevents passage of tissue sample sized solids.

Figure 6:
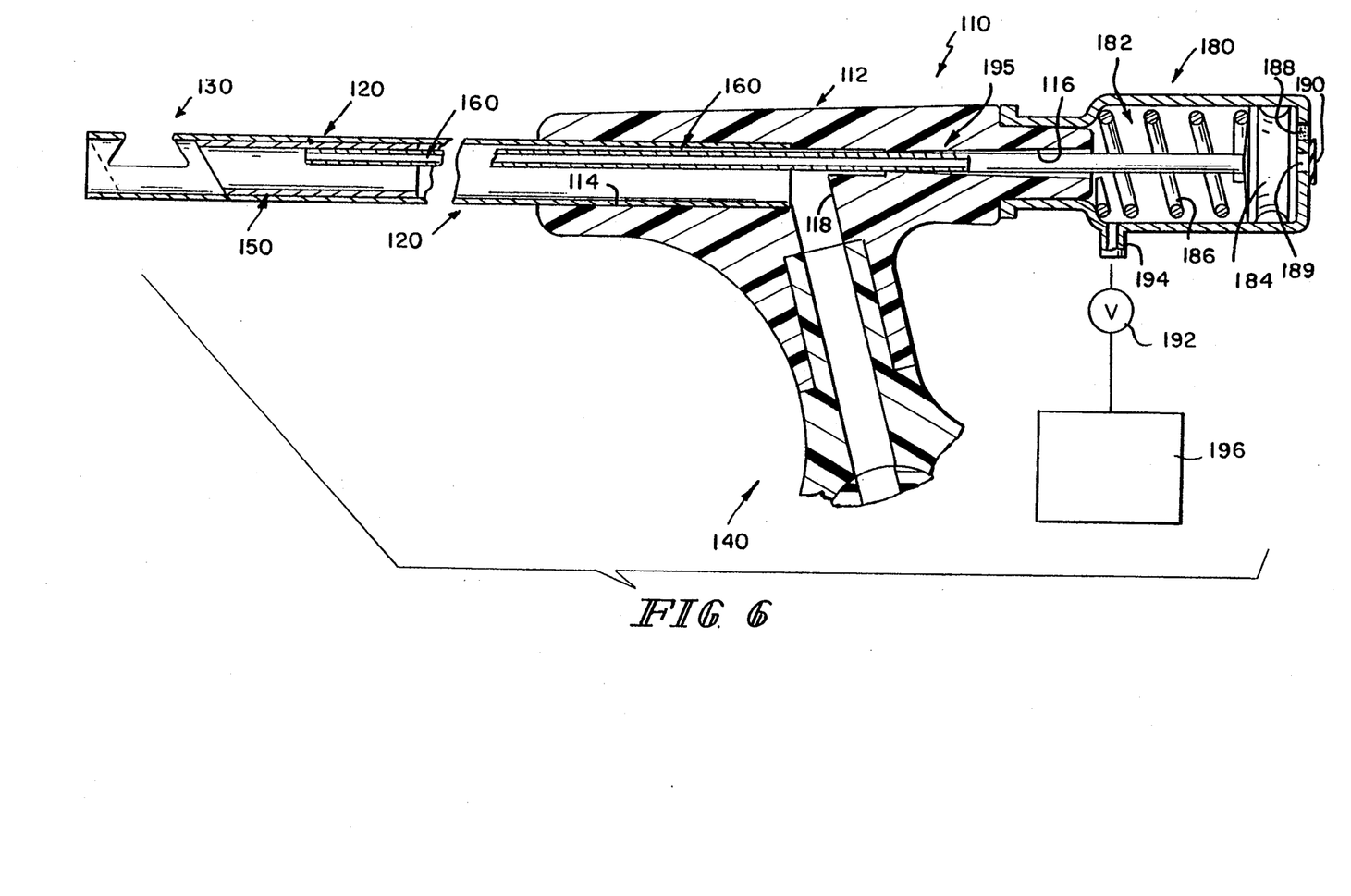
FIG. 6 is a cross sectional side view of a tissue removal assembly including elements similar to that illustrated in FIG. 1, the assembly including a conduit piece, a cannula connected to the conduit piece, with the cannula having a notch into which body tissue can be maneuvered, a tube configured to support a fiber optic cable, a cutter connected to the tube, the cutter being positioned in the cannula to cut tissue inserted through the notch, and movement of the cutter being controlled by a vacuum powered mechanism attached to the conduit piece and connected to reciprocatingly move the tube and attached cutter.

An alternative embodiment of the invention in which movement of a cutter is controlled by application and release of a vacuum is illustrated in FIG. 6. A tissue removal assembly 110 includes a cannula 120 connected to a conduit piece 112 and a valve 140. The conduit piece 112 is formed to define first, second and third channels 114, 116, and 118, with the cannula 120 being inserted into the conduit piece 112 to fit into first channel 114. In addition, like the embodiment of the invention illustrated in FIG. 1, a cutter 150 can be moved through the cannula 120 to alternately block notch 130 or allow passage through the notch 130 of body tissue (not shown).

The cutter 150 is attached to a tube 160 configured to support a fiber optic cable capable of transferring laser energy to an operative site. Although use of a laser is not always required, its ready availability allows a surgeon to select to use the laser alone, the cutter alone, or both the laser and the cutter as necessary to optimize surgical treatment.

The tube 160 passes through the cannula 120 and into conduit piece 112, where it passes in substantially gas tight sliding seal through neck 195 of the second channel 116. The sliding seal in neck 195 can optionally be enhanced by the use of lubricants or low frictional resistance polymeric coatings. Of course, as those skilled in the art will appreciate, breachable elastomeric seals, annular seals, or other conventional sliding seals can be used.

After passing through neck 195, the tube 160 enters chamber 182 of a vacuum powered mechanism 180. The vacuum powered mechanism 180 is a low cost, disposable mechanism attached to the conduit piece 112 to allow a surgeon to control movement of the cutter 150. The chamber 182 of the mechanism 180 is configured to define an air inlet 188, a passageway 189, and a vacuum port 194 for connection by way of valve 192 to a vacuum source 196. Valves such as described in U.S. Pat. No. 5,019,054, to Clement et al., issued May 28, 1991, are preferred, although of course other conventional valves or mechanisms for controlling application of vacuum and allowing admission of air into chamber 182 are also suitable. In other contemplated embodiments a separate valve positioned between the chamber 182 and the vacuum source is not required. As those skilled in the art will appreciate, the vacuum source 196 can be directly controlled to provide pulsatile, oscillatory, or other predetermined suction action to withdraw air from the chamber 182.

The air inlet 188 defined by chamber 182 is normally open to atmosphere, and passageway 189 is sealed by a breachable seal 190 adhesively attached to the chamber 182. The chamber 182 is dimensioned to allow placement of helical spring 186 or other suitable energy storing resilient piece (eg. leaf springs) into the chamber 182. The spring 186 is positioned between a sliding piston 184 and the conduit piece 112. As will be appreciated by those skilled in the art, the position of a spring or resilient piece in the chamber 182 can be varied to accomodate differing spring directions (i.e. biased to resist motion either away or toward the conduit piece 12). In addition, by providing suitable interconnections between the piston 184 and a spring, it is contemplated to mount the spring outside the chamber, rather than inside as illustrated.

The sliding piston 184 is positioned in sliding, gas tight movement in chamber 182. The piston 184 is attached to tube 160, and is configured to have a passageway therethrough (not shown) in fluid communication with the tube 160. Presence of the passageway through the piston 184 allows a surgeon to insert a fiber optic cable (not shown) through the seal 190 and passageway 189, and continue insertion through the passageway of piston 184 into tube 160 for positioning at the surgical site.

Operation of the assembly 110 is similar to operation of assembly 10 illustrated in FIG. 1, with the following difference in cutter actuation. Instead of manually pressing button 66 of assembly 10 to move the cutter 50, use of assembly 10 requires operating valve 192 to open a fluid connection between chamber 182 and vacuum source 196. Air present in chamber 182 rushes out through port 194, causing movement of the piston 184 (or other devices that move in response to pressure changes such as a diaphragm) toward the conduit piece 112. Movement of the piston 184 simultaneously compresses the spring 186 to store energy, and moves the cutter 150 (attached to the piston 184 by tube 160) forward through the notch 130 of the cannula 120, cutting any tissue contained therein. After the cutter has moved forward, the valve 192 can be moved to a position allowing influx of air at normal atmospheric pressure into the chamber 182, which in turn allows release of spring 186 and movement of the piston 184 and attached tube 160/cutter 150 away from the notch 130. The valve 192 can be moved to an open position to repeat the foregoing operation.

Although the invention has been described in detail with reference to certain preferred embodiments, variations and modifications exist within the scope and spirit of the .invention as described and defined in the following claims.

I claim:

1. A surgical lavage assembly for removal of body tissue, the assembly comprising:
    a rigid cannula defining a cannula interior, the cannula having a proximal end and a distal end, the distal end being insertible and accurately positionable into a patient's body, and the rigid cannula defining a cannula opening adjacent the distal end to permit access to the cannula interior for capture of body tissue in the cannula interior;
    a cutter moveable in the cannula and cooperating with the cannula opening for cutting body tissue;
    a conduit piece rigidly attached to the rigid cannula and having a least one channel defined therein in fluid communication with an interior of the cannula for connection to a source of irrigation fluid and suction;
    a means to move the cutter;
    a valve means rigidly connected to the conduit piece for independent actuation to control suction fluid flow in the at least one channel, regardless of movement or lack of movement of the cutter;
    means to actuate the valve means;
    the rigidly connected valve means and conduit piece rigidly attached to the rigid cannula, the rigidly connected valve means and conduit piece having a hand grippable surface for holding and accurately positioning the distal end of the cannula at a specific location in the patient by movement of the rigidly connected valve means, conduit piece and rigid cannula; and
    wherein the means to move the cutter and the means to actuate the valve means are both operable by a hand of a user as it grips the grippable surface to hold and accurately position the distal end of the cannula.

2. The surgical assembly of claim 1 wherein the distal end of the cannula further defines a tip opening to allow fluid communication with the cannula interior, and the cannula opening is positioned between oppositely directed first and second catches configured to assist capture and retention of body tissue in the cannula interior.

3. The surgical assembly of claim 1, wherein the means to move the cutter comprises a push button extending outside the conduit piece.

4. The surgical assembly of claim 3, wherein the means to move the cutter is resiliently biased to withdraw the cutter toward the conduit piece and away from the distal end of the cannula.

5. The surgical assembly of claim 1, wherein the means to move the cutter is resiliently biased to withdraw the cutter toward the conduit piece and away from the distal end of the cannula.

6. A surgical assembly for removal of body tissue, the assembly comprising:
    a rigid cannula defining a cannula interior, the cannula having a proximal end and a distal end, the distal end being insertible and positionable into a patient's body, and the cannula defining a cannula opening adjacent the distal end to permit access to the cannula interior for capture of body tissue in the cannula interior, the rigidity of the cannula causing the distal end thereof to be moved in response to movement of the proximal end;

a cutter defining a passageway and moveable in the rigid cannula for cooperating with the cannula opening for cutting body tissue;

means for moving the cutter;

a conduit piece rigidly attached to the rigid cannula, the conduit piece having at least one channel defined therein in fluid communication with the passageway defined by the cutter for connection to a source of irrigation fluid and suction; suction means connected to the at least one channel for removing body tissue cut by the cutter through the cannula and conduit piece;

valve means rigidly coupled to the rigidly attached conduit piece and rigid cannula for controlling vacuum flow through said one channel;

the rigidly coupled valve means and conduit piece having a handgrip portion for holding and accurately positioning the distal end of the rigid cannula to a desired location in the patient by movement of the handgrip portion;

means to actuate the valve means;

a tool entry conduit located within the cutter and extending outwardly of the conduit piece in a direction away from the cannula for permitting entry of a surgical tool into the conduit piece and the cutter; and wherein both the means for moving the cutter and the means for actuating the valve means can be actuated by a hand gripping the handgrip portion while the hand moves the rigidly attached valve means, conduit piece and rigid cannula to position the distal end of the cannula at the desired location in the patient.

7. The surgical assembly of claim 6, wherein the distal end of the cannula further defines a tip opening to allow fluid communication with the cannula interior, and the cannula opening is positioned between oppositely directed first and second catches configured to assist capture and retention of body tissue in the cannula interior.

8. The surgical assembly of claim 6, wherein the tool entry conduit is fixedly attached to the moveable hollow cutter; and wherein means are provided to move the tool entry conduit to cause the cutter to move in the cannula interior to cut body tissue therein.

9. The surgical assembly of claim 8, wherein the means to move the cutter comprises a push button extending outside the conduit piece.

10. The surgical assembly of claim 8, wherein the valve means is connected to the conduit piece for independent actuation to control suction in the at least one channel, regardless of movement or lack of movement of the cutter.

11. The surgical assembly of claim 6, wherein the means to move the tool entry conduit includes a seal for sealingly engaging the tool conduit with any surgical tool inserted therein.

12. The surgical assembly of claim 11, wherein the means to move the cutter comprises a push button extending outside the conduit piece.

13. The surgical assembly of claim 11, wherein the means to move the cutter is resiliently biased to withdraw the cutter toward the conduit piece and away from distal and of the cannula.

14. The surgical assembly of claim 11, wherein the valve means is connected to the conduit piece for independent actuation to control suction in the at least one channel, regardless of movement or lack of movement of the cutter.

15. The surgical assembly of claim 8, wherein the means to move the cutter is resiliently biased to withdraw the cutter toward the conduit piece and away from distal and of the cannula.

16. The surgical assembly of claim 6, wherein the valve means is connected to the conduit piece for independent actuation to control suction in the at least one channel, regardless of movement or lack of movement of the cutter.

17. A lavage assembly for laparoscopy surgery, irrigation, and suction, and removal of body tissue, the assembly comprising:

a cannula defining a cannula interior, the cannula having a proximal end and a distal end, the distal end being insertible into a patient's body, and the cannula defining a notch in the distal end to permit access to the cannula interior for capture of body tissue in the cannula interior;

a cutter moveable in the cannula for cutting body tissue entering the notch;

means for moving the cutter extending into the cannula;

a valve connected to the cannula for independent actuation to control irrigation and suction fluid flow in the cannula, regardless of movement or lack of movement of the cutter; and wherein the cannula and valve are integrated into a rigid structure to be held in one hand.

18. The surgical assembly of claim 17, wherein the means for moving the cutter comprises a means which may be operated by a digit of the one hand holding the valve.

19. The surgical assembly of claim 6, wherein the means to move the cutter is resiliently biased to withdraw the cutter away from the distal end of the cannula such that a push action against the resilient bias moves the cutter for cutting.

20. The surgical assembly of claim 6 wherein the cutter is hollow and the cutter passageway is a duct extending internally of the cutter.

21. The surgical assembly of claim 6 wherein the handgrip portion for gripping the rigidly coupled valve means and conduit piece is a surface surrounding the valve means.

22. The surgical assembly of claim 6 where the valve means is located in the conduit piece.

23. The surgical assembly of claim 20 wherein the rigid cannula is open at its distal end to allow fluid communication into the cannula interior.

24. The surgical assembly of claim 6 wherein the handgrip portion is configured as a pistol grip.

25. The surgical assembly of claim 8 wherein the handgrip portion is configured as a pistol grip.

26. The surgical assembly of claim 6 wherein the interior of the rigid cannula allows for passage of liquid into the body as well as withdrawing of body tissue.

27. The surgical assembly of claim 1 wherein the handgrip portion for gripping the rigidly coupled valve means and conduit piece is a surface surrounding the valve means.

28. The surgical assembly of claim 1 where the valve means is located in the conduit piece.

29. The surgical assembly of claim 1 wherein the rigid cannula is open at its distal end to allow fluid communication into the cannula interior.

30. The surgical assembly of claim 17 wherein the rigid structure of the cannula and valve means has a handgrip portion to allow the user's hand to grip the rigid structure for positioning of the cannula.

31. The surgical assembly of claim 30 wherein the handgrip portion is a surface surrounding the valve means.

32. The surgical assembly of claim 17 wherein the rigid cannula is open at its distal end.

* * * * *